Aug. 21, 1956 H. J. GROOTENDORST Plant Pat. 1,506
EXOCHORDA MACRANTHA HYBRID PLANT
Filed July 11, 1955
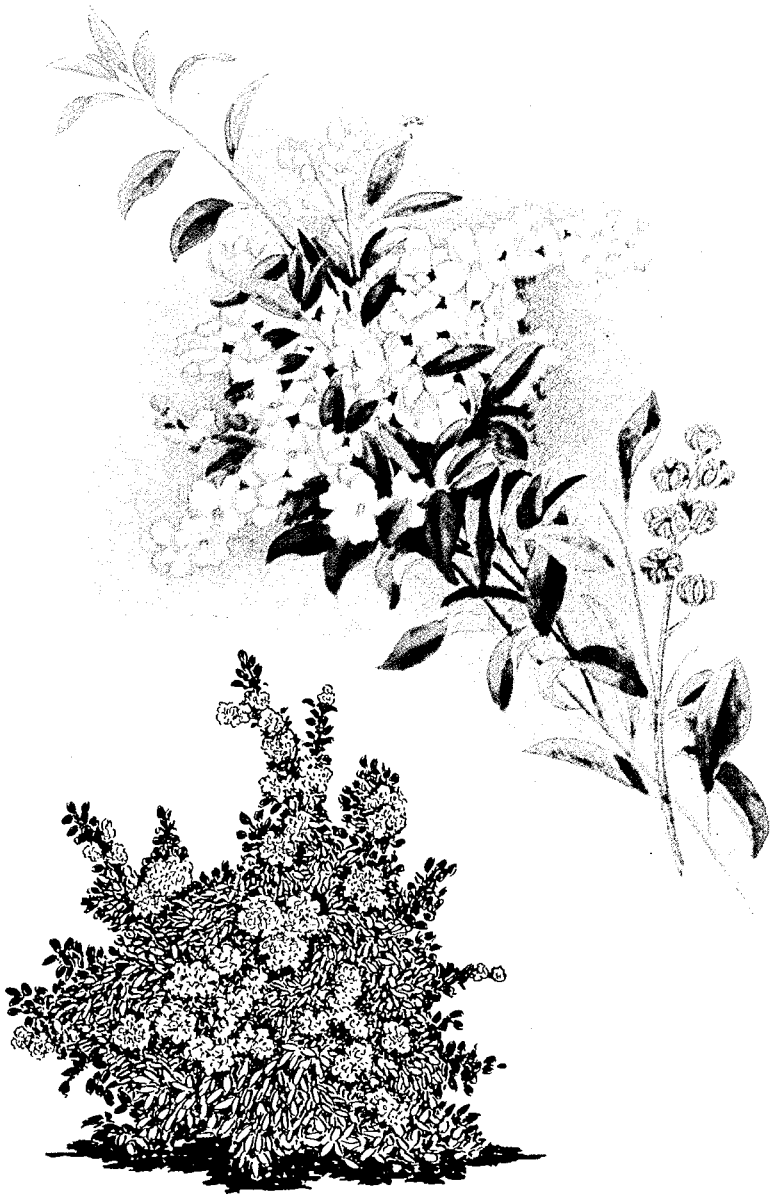
WITNESS
Gadison E. Avery
INVENTOR
Herman Johannes Grootendorst,
by: John H. Brewer Jr.,
his ATTY.

United States Patent Office

Plant Pat. 1,506
Patented Aug. 21, 1956

1,506

EXOCHORDA MACRANTHA HYBRID PLANT

Herman Johannes Grootendorst, Boskoop, Netherlands, assignor to John J. Grullemans, Cleveland, Ohio Application July 11, 1955, Serial No. 521,431

1 Claim. (Cl. 47—60)

This invention relates to a new and distinct variety of *Exochorda macrantha* hybrid plant.

The new variety is illustrated in the drawings in which:

The large colored view at the upper part of the drawing illustrates a typical flower stalk of the plant bearing leaves, blossoms and seed pods; and The black and white sketch at the lower part of the drawing illustrates the shape of the plant as a whole.

The *Exochorda macrantha* hydrib of the present invention is a cross between an *Exochorda macrantha* as the seed or pistillate parent and an *Exochorda racemosa* as the pollen or staminate parent.

The *Exochorda macrantha* seed parent, is a hybrid in turn, resulting from a cross between an *Exochorda racemosa* and an *Exochorda korolkowii*. The *Exochorda racemosa* pattern or staminate parent is a species.

The crossing of the parent was by hand pollination from a selected dwarf plant of the male parent onto the female parent. The present plant was selected as the most dwarf one of the progeny of this crossing.

The new variety was first developed by me in Oudenbosch, Holland, and was first asexually reproduced by me by grafting hardwood cuttings of the plant stock onto roots in Oudenbosch, Holland.

Some of the asexually reproduced plants have been sent to the United States and are being grown there successfully.

The original plant has a root which is openly branched and of average size. The plant generally is deep-rooted having the usual lateral spread of Exochorda plants.

The exposed plant is a hardy, woody shrub which is unusually dense, and bushy for an Exochorda plant. It has a somewhat rounded top with occasional protruding branches.

Compared to prior Exochorda plants of the same age, the present plant is about 4 feet high and 4 feet across whereas the prior plants are from 10 to 12 feet high when about 4 feet across.

The plant is generally globular in vertical silhouette with the lateral branches recurvant. As a whole, it is very dwarf for an Exochorda plant.

It prefers as a growing site the full sun with no shade whatever and normally well drained soil but otherwise is indifferent to exposure and type of soil.

The main stalks of the plant are curved and tough and are adequate to support the foliage and bloom well. Their color is that which is usual for Exochorda plants. The plant generally grows from the root with a single main stalk with a large number of lateral branches, the main stalk being relatively straight and upright and the lateral branches recurvant.

The foliage has the usual appearance for plants of this variety and is abundant, the leaves being of average size, shape, thickness and texture. On their upper surfaces the leaves are a green comparable to Maerze and Paul Chart Plate No. 21–L–8 and on their under surfaces they are an Asphodel green comparable to Maerze and Paul Chart Plate No. 21–J–5. Their persistency on the plant is excellent.

The plant blooms well in a sunny location, in a dry, hot season, and in well drained soil. At times it blooms as early as May but generally in more northerly locations, such as in Canada, it blooms at the end of June. In Holland, it usually blooms after June.

The buds display no unusual characteristics for an Exochorda plant.

The blooms are of the average size, being from 1½ to 2 inches in diameter. The blossoms are borne generally in racemes but, on occasion, single or couples of blossoms are borne on the side twigs. Each raceme includes about 10 to 15 blossoms which is about twice what is normal for an *Exochorda macrantha* plant. The permanence of the blossoms on the plant is very good. They remain in good condition for as long as two weeks. However, the cut blooms do not survive well.

The petals of the plant show no trace of color and are what may be termed a "dead white." The petals are of average size and appearance.

The blooms have no aroma.

The fruit is the usual five angled capsule common for Exochorda plants. The plant adapts itself well to different growing locations and is well adapted for the climates such as found in northeastern United States and for any good garden soil.

Having shown and described my new variety of *Exochorda macrantha* hybrid plant, I claim:

A new and distinct variety of *Exochorda macrantha* hybrid plant substantially as herein described and illustrated, characterized particularly by its dwarfness, compactness and recurvant branches, its free flowering, and the unusually large number of blossoms constituting each raceme.

No references cited.